(12) United States Patent
Park et al.

(10) Patent No.: US 7,083,968 B2
(45) Date of Patent: Aug. 1, 2006

(54) MICROORGANISM OF SERRATIA FAMILY, ISOLATION METHOD AND THE PREPARATION METHOD OF LIGNIN LYASES USING THIS

(75) Inventors: Ho Yong Park, Taejon-si (KR); Ki Duk Kim, Taejon-si (KR); Dong Ha Shin, Taejon-si (KR)

(73) Assignee: Insect Biotech Co., Ltd. (KR)

( * ) Notice: Subject to any disclaimer, the term of this patent is extended or adjusted under 35 U.S.C. 154(b) by 0 days.

(21) Appl. No.: 10/481,233

(22) PCT Filed: Jul. 31, 2001

(86) PCT No.: PCT/KR01/01300

§ 371 (c)(1),
(2), (4) Date: Dec. 16, 2003

(87) PCT Pub. No.: WO05/102995

PCT Pub. Date: Dec. 27, 2002

(65) Prior Publication Data

US 2004/0241846 A1 Dec. 2, 2004

(30) Foreign Application Priority Data

Jun. 20, 2001 (KR) .............................. 2001/35046

(51) Int. Cl.
*C12N 1/12* (2006.01)
(52) U.S. Cl. .................... 435/252.1; 435/243
(58) Field of Classification Search ................ 435/243, 435/252.1
See application file for complete search history.

(56) References Cited

OTHER PUBLICATIONS

Field, Jim A., et al., Screening for Ligninolytic Fungi Applicable to the Biodegradation of Xenobiotics, Tibtech Feb. 1993 (vol. 11).
Eggert, Claudia, et al., The Ligninolytic System of the White Rot Fungus *Pycnoporus cinnabarinus*: Purification and Characterization of the Laccase, Applied and Environmental Microbiology, Apr. 1996, p. 1151-1158.
Schliephake, Kirsten, et al., Laccase Variation During Dye Decolourisation in a 200 L Packed-Bed Bioreactor, Biotechnology Letters, vol. 18, No. 8 (Aug.) pp. 881-886, Received as revised May 28.
Kuhnigk, T., et al., Degradation of dimeric lignin model compounds by aerobic bacteria isolated from the hindgut of xylophagous termites, J. Basic Microbiol. 37 (1997) 3, 205-211.
Rhoads, T. L., et al., Investigation of the lignin-degrading activity of *Serratia marcescens*: biochemical screening and ultrastructural evidence, Can. J. Microbiol. 41: 592-600 (1995).

Temp, U., et al., Cloning and characterization of a second laccase gene from the lignin-degrading basidiomycete *Pycnoporus cinnabarinus*, Gene 236 (1999) 169-177.
Tuncer, M., et al., Optimization of extracellular lignocellulolytic enzyme production by a thermophilic actinomycete *Thermomonospora fusca* BD25, Enzyme and Microbial Technology 25 (1999) 38-47.
Hilden, L., et al., Do the extracellular enzymes cellobiose dehydrogenase and manganese peroxidase form a pathway in lignin biodegradation, FEBS Letters 477 (2000) 79-83.
Leonowicz, A., et al., Biodegradation of Lignin by White Rot Fungi, Fungal Genetics and Biology 27, 175-185 (1999).
Chivukula M., et al., Phenolic Azo Dye Oxidation by Laccase from Pyricularia oryzae, Applied and Environmental Microbiology, Dec. 1995, p. 4374-4377.
Kato, K., et al., Degradation of lignin compounds by bacteria from termite guts, Biotechnology Letters vol. 20, No. 5, May 1998. pp. 459-462.
Perry, C.R., et al., The structure of laccase protein and its synthesis by the commercial mushroom *Agaricus bisporus*, Journal of General Microbiology (1993), 139, 171-178.
Barbosa, A.M., et al., Veratryl alcohol as an inducer of laccase by an ascomycete, *Botryosphaeria* sp., when screened on the polymeric dye Poly R-478, Letters in Applied Microbiology 1996, 23, 93-96.
Rodriguez, C.S., et al., Laccase production in semi-solid cultures Phanerochaete chrysosporium, Biotechnology Letters, vol. 19, No. 10, Oct. 1997, pp. 995-998.
Fortina, MG, et al., Production of laccase by Botrytis cinerea and fermentation studies with strain F226, Journal of Industrial Microbiology (1996) 17, 69-72.
Lee, Y.S., Qualitative Evaluation of Ligninolytic Enzymes in Xylariaceous Fungi, J. Microbiol. Biotehnol. (2000), 10(4), 462-469.

(Continued)

*Primary Examiner*—Robert A. Zeman
(74) *Attorney, Agent, or Firm*—Lucas & Mercanti, LLP

(57) ABSTRACT

The present invention relates to a novel microbe belonging to Serratia family, its isolation method and the preparation method using it. More particularly, the present invention relates to a microorganism of Serratia family producing laccase, lignin peroxidase and Mn-dependent-peroxidase which are the kinds of lignin lyases, and a method for separating the microbe from insect gut, as well as a method for preparing laccase, lignin peroxidase and Mn-dependent-peroxidase. The microorganism of the present invention can be used not only in the treatment of industrial sewage and harmful environmental substance but also in oil degradation, in biological bleaching of pulp since it can produce lignin lyases. More over, the microbe can also be used effectively in industry of preparing fuel, forage and other chemicals through lignin degradation.

3 Claims, 5 Drawing Sheets

OTHER PUBLICATIONS

Arora, D.S., Laccase production by some white rot fungi under different nutritional conditions, Bioresourse Technology 73 (2000) 283-285.

Hirano, T., et al., Degradation of Bisphenol A by the Lignin-Degrading Enzyme, Manganese Peroxidase, Produced by the White-rot Basidiomycete, *Pleurotus ostreatus*, Biosci. Biotechnol. Biochem., 64 (9), 1958-1962, 2000.

Mansur, M., et al., Identification of a Laccase Gene Family in the New Lignin-Degrading Basidiomycete CECT 20197, Applied and Environmental Microbiology, Jul. 1997, p. 2637-2646.

MICROORGANISM OF SERRATIA FAMILY, ISOLATION METHOD AND THE PREPARATION METHOD OF LIGNIN LYASES USING THIS

This patent application claims the benefit of priority from Korean Patent Application No. 2001-0035046 filed Jun. 20, 2001 through PCT Application Ser. No. PCT/KR01/01300 filed Jul. 31, 2001, the contents of each of which are incorporated herein by reference.

FIELD OF THE INVENTION

The present invention relates to a novel microbe belonging to Serratia family, its isolation method and the preparation method using it. More particularly, the present invention relates to a microorganism of Serratia family producing laccase, lignin peroxidase and Mn-dependent-peroxidase which are the kinds of lignin lyases, and a method for separating the microbe from the gut of insect, as well as a method for preparing laccase, lignin peroxidase and Mn-dependent-peroxidase. The microorganism of the present invention can be used not only in the treatment of industrial sewage and harmful environmental substance but also in oil degradation, in biological bleaching of pulp since it can produce lignin lyases. Moreover, the microbe can also be used effectively in industry of preparing fuel, forage and other chemicals through lignin degradation.

BACKGROUND

The present invention relates to a novel microbe belonging to Serratia family, its isolation method and the preparation method using it. More particularly, the present invention relates to a microorganism of Serratia family producing laccase, lignin peroxidase and Mn-dependent-peroxidase which are the kinds of lignin lyases, and a method for separating the microbe from the gut of insect, as well as a method for preparing laccase, lignin peroxidase and Mn-dependent-peroxidase.

Lignin is the second most abundant material on earth after cellulose, and it is a kind of macromolecular compound existing in middle lamella and first cell wall of plant (Munir, T., et al., *Enzyme and Microbial Technol.,* 1999, 25, 38–47). Lignin takes 15–35% of a total dried wood weight and exists in middle lamella between cell membrane as a high-molecular aromatic condensation compound while some of lignin exists in cell membrane. Lignin has various structures, but generally it has the structure of propylbenzene derivatives having substituent such as methoxyl or hydroxyl group in aromatic ring. Due to its complicated structure and stability, lignin has significant resistance against biological attacks. None of organism, though, using this as only carbon. source for their growth has been known(Higuchi, *Experientia,* 1982, 38, 159–166; Janshekar, H. and Feichter, A., *Advances in Biochemical Engineering/Biotechnol.,* 1983, 27, 119–178).

Precursors composing lignin are ρ-coumaric alcohol, coniferyl alcohol, sinapyl alcohol and cinnamyl alcohol. The composition ratio of these precursors varies with the type, age and tissue of a plant. When the above mentioned precursors are going under oxidation by peroxidase existing in living matter, free radicals are formed as an intermediate product. These formed free radicals respond each other to be a pair and polymerized resulting in a form of macromolecule having phenyl-propane as a basic unit. That macromolecule is lignin (Hilden, L., et al., *FEBS Letters,* 2000, 477, 79–83; Leonowicz, A., et al., *Fungal Genetics and Biology,* 1999, 27, 175–185). Lignin is obtained as an aromatic compound through the process of de-polymerization of phenyl propanoid, a very complicated molecular unit, and becomes an important composition of cell wall of higher plant which provides power to resist outside attack.

Lignin peroxidase, Mn-dependent-peroxidase and laccase are the kind of lignin lyases.

As a polyphenol oxidase containing copper, laccase is called blue copper protein or blue copper oxidase and able to oxidize and resolve many toxic materials like phenol compound which is difficult to be resolved. With this resolving power, laccase effectively eliminates lignin from wood, which helps to enhance the quality of pulps.

Kraft process has been used to remove lignin from pulps. With this method about 90% of lignin can be extracted from pulps by cooking and by using NaOH, and the rest 10% of lignin is removed by using chlorine or chlorine dioxide. When chlorine compound is used to eliminate lignin, however, it co-responses with lignin to make chlorolignol, a chloro-organic compound, which is not only very slowly resolved in nature but also can cause problems in the immune and nervous systems of living matter. Thus, worldwide efforts have been made to legally prohibit against producing pollutants through lignin resolving process. The chemical resolving method of lignin has many problems economically and environmentally since this method consumes a lot of chemical compounds and requires lots of energy, and also produces many toxic pollutants containing chlorolignol (Boominathan and Reddy, *Fungal Degration Lignin,* 1992, 763–822).

When lignin is treated with lignin lyases, less energy and small amount of compounds are required and production of environmental pollutants could be reduced. Besides, lignin lyase is very important in the aspect of environmental protection since it exists in various types of natural systems and can resolve the aromatic compounds which are harmful for human and nature (Field, J. F., et al., *Trend in Biotechnol.,* 1993, 11, 44–49).

Degradation-difficult organics such as saw dust, shavings, bark, waste ash, rice husk, rice straw, wheat straw, seed coat of beans, falling leaves, waste crop of oak mushrooms and other mushrooms are dejected in the field of agriculture and in other industries, and the carbon content ratio of those is 40–100%. Lignin takes 15–40% of their components, and lignin lyases resolve them effectively. Products after treated with lignin lyases can be used as organic fertilizer, which means industrial waste could be reused effectively.

Lignin lyases are also used in degradation of dye and decoloration of textile. More than 10,000 types of dyes are produced in the annual amount of $7 \times 10^5$ tons world widely from dyeing plant and dye-production plant. Synthetic dyes containing unresolving functional group such as azo group, nitro group and sulfon group are degradation-difficult toxic materials. Those still have been treated with physical, chemical methods which cost a lot and cause environmental contamination since there has been no other effective useful way so far. Thus, active studies have been made for the biological treatment of those degradation-difficult toxic materials using microorganism which is economical and has no need to worry about secondary contamination (Oh, K. G., et al., *Kor. J. Appl. Microbiol. Biotechnol.,* 1999, 6, 500–508). There is a report concerning degradation of phenol-azo dye using laccase produced from *Pyricularia oryzae*(Chivukula, M. and V. Renganathan, *Appl. Environ. Microbiol.,* 1995, 61, 4374–4377). And there is another report concerning degradation of aromatic compound using laccase produced from *Trametes versicolor*(Nicklas, *Appl. Environ. Microbiol.,* 1989, 31, 70).

As of today, most of the reported microorganisms that produce lignin lyases are the fungus. The reported fungus are *Agaricus bisporus* belongs to white rot fungus, *Pholiota aegerita, Podospora anserine, Trametes versicolor, Pleurotus ostreatus,* and *Phanerochaete chrysosporium,* etc. (Chivukula, M. and V. Renganathan, *Appl. Environ. Microbiol.,* 1995, 61, 4374–4377; Nicklas, *Appl Environ. Microbiol.,* 1989, 31, 70; Perry, C. R., et al., *J. General Microbiol.,* 1993, 139, 171–178; Rodriguez, C. S., et al., *Biotech. Lett.,* 1997, 19, 995–998), and the reported bacteria are *Burkholdera cepacia* and *Azospirillum lipoferum,* etc. (Kinya, K. S., et al., *Biotechno. Lett.,* 1998, 20, 459–462; Thurston, C. F., *Microbiology,* 1994, 140, 19–26).

The fungus such as white rot fungus grow slowly, and are not easily genetically mutated, so that it takes long time to culture and have difficulty in genetical uses. Meanwhile, bacteria are much useful sine they grow fast and are mutated easily. Degradation of lignin using fungus is too slow to use in industry because it can be induced only when carbon and nitrogen source are deficient. And fungus metabolize cellulose fiber as their first nutrient resulting in the reduction of the quality of pulp and yield of pulp production. Therefore, it is urgent and important to select a proper bacterium which can produce lignin lyases.

To overcome the foregoing and other disadvantages, we, the inventors of the present invention, have attempted to select a proper microorganism, a bacterium, producing lignin lyases which can resolve or treat degradation-difficult materials which cause many environmental problems. To select a proper microorganism, the present inventors have separated a microorganism from the gut of insect such as *Sympetrum depressiusculm,* and have confirmed that it belongs to Serratia family. And finally, the present invention is performed by verifying that this microorganism produces one or more lignin lyases among laccase, lignin peroxidase and Mn-dependent-peroxidase.

SUMMARY OF THE INVENTION

It is an object of this invention to provide a novel microorganism of Serratia family producing lignin lyases.

It is another object of this invention to provide a preparation method of the microorganism.

It is a further object of this invention to provide a preparation method of lignin lyases using thereof.

BRIEF DESCRIPTION OF THE DRAWINGS

L: dealkaline lignin, VA: vanillic acid,
V: vanillin, G: guaiacol,
ρ: ρ-coumaric acid, PH: phenol,
LB: LB medium

DETAILED DESCRIPTION OF PREFERRED EMBODIMENTS

To accomplish those objects, the present invention provides a novel microorganism of Serratia family producing laccase, lignin peroxidase and Mn-dependent-peroxidase which are all lignin lyases.

The present invention also provides a preparation method of the microorganism from insect gut.

This invention also provides a preparation method of lignin lyases from the culture supernatant of the microorganism culture.

Hereinafter, the present invention is described in detail.

In one aspect, the present invention provides a novel microorganism of Serratia family producing laccase, lignin peroxidase and Mn-dependent-peroxidase which are all lignin lyases.

The microorganism of the present invention has been isolated from gut of insect such as *Sympetrum depressiusculm*. After contaminants of the surface of the insect body were removed, insect gut was taken out and crushed by crusher. A microorganism resolving lignin was selected from the extract obtained crushed gut by colony activity staining method using lignin resolving power. The microorganism was cultured on solid medium containing lignin for 24 hours and lignin activity staining was performed. As a result, the present inventors verified that white circle was formed by the degradation of lignin.

The present inventors have confirmed that the microbe has homology with Serratia (approximately 80% of similarity) through the analysis of basic enzyme activity, usage of carbon source, acid production from carbon source, nitrogen gas production and composition of cellular fatty acid. More specifically, the present inventors have isolated genomic DNA therefrom and analyzed base sequence with the obtained 16S rDNA, through which the present inventors have confirmed that the microorganism belongs to Serratia family and shows plenty of similarity to *Serratia marcescens*. The microorganism, however, is a little different from typical *Serratia marcescens*. Thus, microorganism of the present invention was named as "*Serratia marcescens* HY-5" and deposited at Gene Bank of Korea Research Institute of Bioscience and Biotehnology on May 22, 2001 (Accession No: KCTC 1009BP).

The present invention also provides a preparation method of the microorganism including steps as follows; 1) crush insect gut, 2) culture the extract on the proper medium, 3) select a microorganism having lignin degradation activity.

This invention also provides a preparation method of lignin lyases from the culture supernatant of the microorganism culture. Laccase, lignin peroxidase and Mn-dependent-peroxidase are the kinds of lignin lyase.

Figure 4:
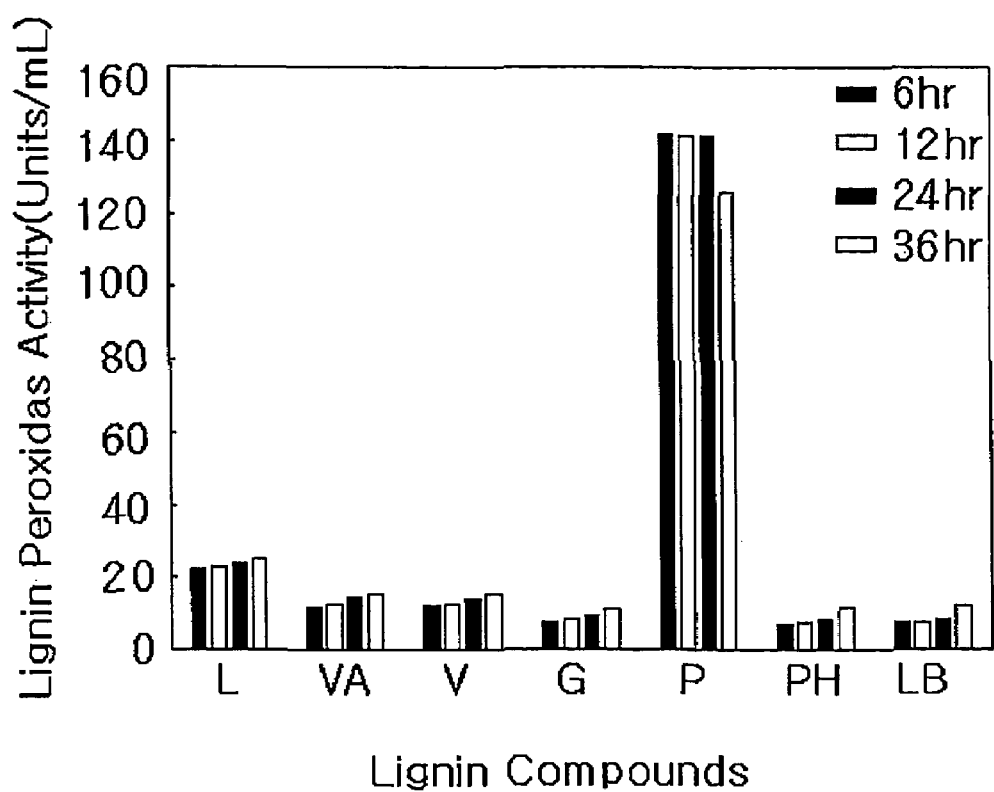
FIG. 4 is a graph showing the acceleration of lignin peroxidase production by addind aromatic compounds.
Figure 5:
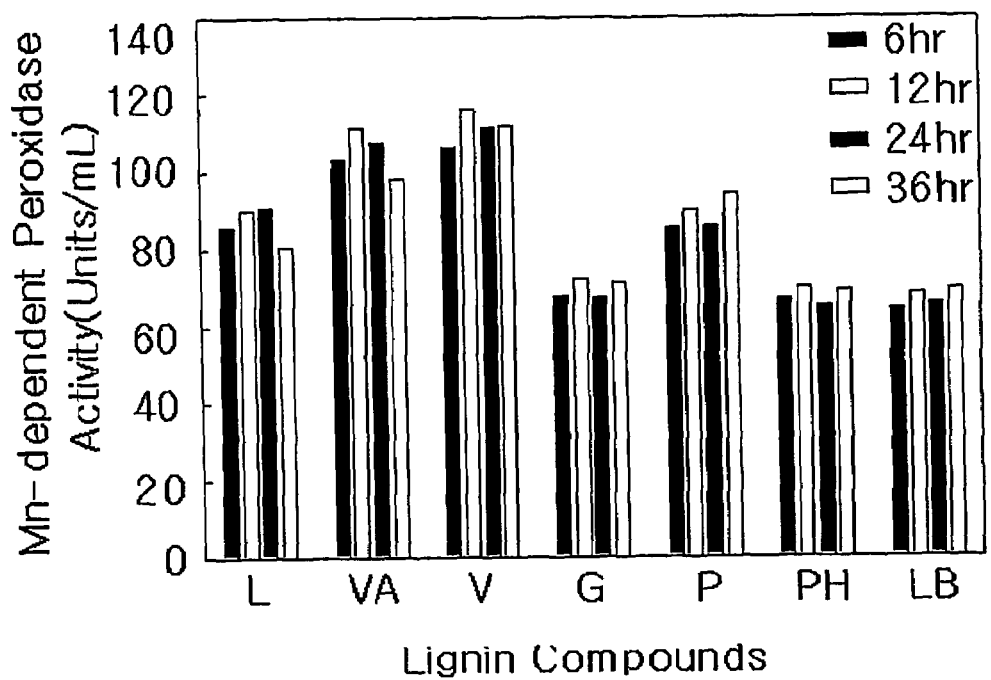
FIG. 5 is a graph showing the acceleration of Mn-dependent-peroxidase production by adding aromatic compounds.
L: dealkaline lignin, VA: vanillic acid,
V: vanillin, G: guaiacol,
ρ: ρ-coumaric acid, PH: phenol,
LB: LB medium

The present inventors investigated about the possibility whether various types of aromatic compounds could increase the production of lignin lyases. As a result, dealkaline lignin induced about two folds as high activation of laccase as other lignin compounds did (FIG. 3), ρ-coumaric acid induced seven-fold high activation of lignin peroxidase than other aromatic compounds did (FIG. 4), and vanillin and vanillic acid induced 1.5-fold high activation of Mn-dependent-peroxidase than other aromatic compounds did (FIG. 5).

EXAMPLES

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Isolation and Identification of the Microorganism

<1-1> Isolation of the Microorganism

In order to get rid of contaminants on the surface of insect body, the insect like *Sympetrum depressiusculm* was dipped in 70% (W/W) ethanol for one or two minutes and washed with distilled water twice. From the washed insect body, gut was taken out and put into PBS (phosphate buffered saline, 0.8% NaCl, 0.02% KCl, 0.144% $Na_2HPO_4$, 0.024% $KH_2PO_4$). Gut in PBS was crushed and extracted. The obtained extract was diluted to $10^{-5}$ and cultured in LB medium for 24–48 hours. The cultured microorganism was moved onto solid medium containing lignin and colony activity staining method was performed. The microorganism forming white ring by lignin degradation was selected.

<1-2> Identification of the Microorganism

The selected microorganism was analyzed by physiological and biochemical methods.

As a result, the microorganism of the present invention was confirmed to produce β-galactosidase, β-glucosidase, lysine dicarboxidase, ornitine dicarboxidase and urease. It also reduced nitrate to nitrite, but it showed negative reaction against oxidase (Table 1). In addition, it produced acid from alcoholic carbohydrate such as manitol, inositol and sorbitol, etc.

TABLE 1

| Characteristics | Reactiviy |
|---|---|
| β-galactosidase | + |
| β-glucosidase | + |
| Oxidase | − |
| Arginine dihydrolase | − |
| Lysine dicarboxidase | + |
| Ornitine dicarboxidase | + |
| Triptophane diaminase | − |
| Urase | + |
| Indole production | − |
| Hydrogen sulfide production | − |
| Aceton production | + |
| Citrate production | + |

And, the microorganism of the present invention could ferment using twin-40, twin-80, fructose, sorbitol, zylose, cunic acid, glycerol, inosine, proline, alanine and citric acid, but it could not use glycogen, cellulose, lactose and leucine for fermentation.

From the analysis of fatty acid of the microorganism of the present invention, it was confirmed that its major fatty acid consists 32.3% of saturated fatty acid having 16 carbons, 12% of cyclo-saturated fatty acid having 18 carbons and 13% of complex having 18 carbons (Table 2).

TABLE 2

| Type of Fatty Acid | Composition (%) |
|---|---|
| C12:0 | 4.1 |
| C14:0 | 4.9 |
| C14:0 2OH | 3.3 |
| C16:0 | 32.3 |
| C17:0 cyclo | 11.9 |
| C18:1 w7c | 13.3 |
| C19:0 cyclo w8c | 2.1 |

Based on physiological and biochemical analysis thereof, the microorganism of the present invention was confirmed to have 80% of similarity to Serratia family.

In order to identify more precisely, the present inventors analyzed base sequence of ribosome small subunit gene. Particularly, genomic DNA was separated by using the Rochell's method (Rochell, P. A., et al., *FEMS Microbiol. Lett.*, 1992, 100, 59–62), and 16S rDNA was synthesized by PCR. The base sequence of the synthesized DNA was determined by using Tag Dye Deoxy Terminator Cycle Sequencing Kit. As a result of database analysis on the decided base sequence using NCBI (National Center for Biological Information) BLAST, the microorganism was confirmed to have similarity to *Serratia marcescens* among Serratia family. However, it had a little difference from the typical *Serratia marcescens*, so that the microorganism of the present invention was finally named as *Serratia marcescens* HY-5.

The above-mentioned microorganism of the present invention was deposited at Gene Bank of Korea Research Institute of Bioscience and Biotechnology on May 22, 2001 (Accession No.: KCTC 1009BP).

Example 2: Lignin Lyase Production of the Separated Microorganism

Figure 1:
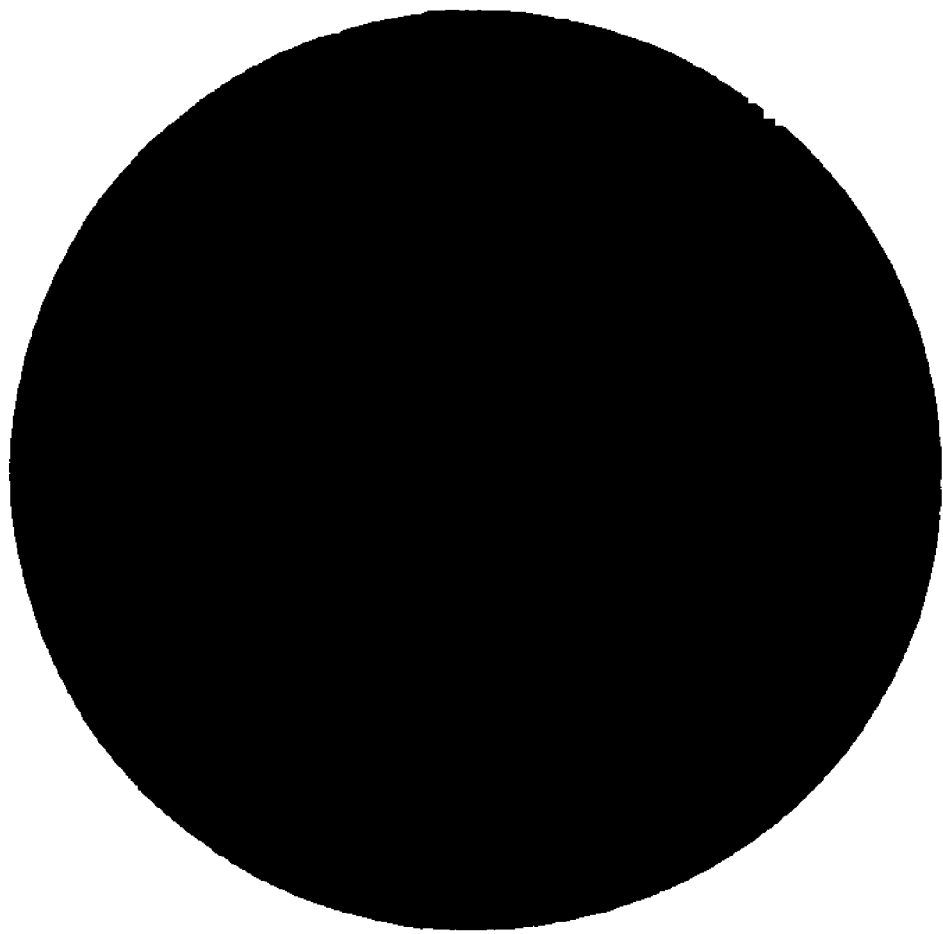
FIG. 1 is a photograph showing the microorganism of the present invention resolves lignin on the medium containing lignin.

To verify whether the microorganism of the present invention produces lignin lyases, simple plate test (Sundman, V. and L. Nase, *Paper och. Tra.*, 1971, 53, 71–76) was performed. Particularly, the microorganism was cultured for 24–48 hours on solid medium made from basic medium (0.5% glucose, 0.5% $NH_4$-tartrate, 0.1% malt extract, 0.001% CaCl, 0.01% NaCl, 0.001% $FeCl_3$) on which 0.025–0.1% lignosulfonate was added. Thereafter the microorganism grown up on the medium was washed with distilled water and the reagent made by 1% $FeCl_3$ and 1% $K_3[Fe(CN)_6]$ with the same amount each was treated on agarose medium, resulting that transparent zone was formed around colony of the microorganism(FIG. 1). This method was to observe whether $FeCl_3$ and $K_3[Fe(CN)_6]$ could response to phenol group of resolved lignin, which finally showed clearly that the microorganism of the present invention produced lignin lyases for the degradation of lignin.

Example 3: Enzyme Activity of Lignin Lyases

<3-1> Enzyme Activity of Laccase

Enzyme activity of laccase was measured by using culture supernatant of the microorganism as coenzyme source.

Particularly, supernatant was obtained by centrifugation of the culture fluid with 13,000 rpm for 5 min. at 4° C. Then, the obtained culture supernatant was mixed with 0.1 M of sodium acetate buffer (pH 5.0), and 0.5 mM of ABTS(2,2-azio-bis(3-ethylbenzthiazoline-6-sulfornic acid) was added thereto for inducing enzyme reaction, and finally, the difference of absorbance was measured at 420 nm for 1 minute. The activation unit of enzyme was decided as the amount of enzyme oxidizing 1 μmole of ABTS per minute.

As a result, it was confirmed that the microorganism of the present invention produced 254 units of laccase when it was cultured for 12 hours on the basic medium, and 300 units when it was cultured for 24 hours.

<3-2> Enzyme Activity of Lignin Peroxidase

Enzyme activity of lignin peroxidase was measured by using culture supernatant obtained in <3-1> as coenzyme source. For enzyme reaction, the culture supernatant was mixed with 100 mM of sodium tartrate buffer (pH 3.0) and 2 mM of veratryl alcohol, and 0.5 mM of $H_2O_2$ was added thereto. Then, the difference of absorbance was measured at 310 nm for 1 minute. The activation unit of enzyme was decided as the amount of enzyme oxidizing 1 μmole of veratryl alcohol into veratyl aldehide per minute.

As a result, it was confirmed that the microorganism of the present invention produced 64.9 units of lignin peroxidase when it was cultured for 12 hours on the basic medium, and 66 units when it was cultured for 24 hours.

<3-3> Enzyme Activity of Mn-dependant Peroxidase

Enzyme activity of Mn-dependant peroxidase was measured by using culture supernatant obtained in <3-1> as coenzyme source. For enzyme reaction, the culture supernatant was mixed with 100 mM of sodium lactate buffer(pH 4.5) and 0.1 mM of $MnSO_4$, and 0.1 mM of $H_2O_2$ was added thereto. Then, the difference of absorbance was measured at 240 nm for 1 minute. The activation unit of enzyme was decided as the amount of enzyme oxidizing $Mn^{2+}$ into $Mn^{3+}$ per minute.

As a result, it was confirmed that the microorganism of the present invention produced 10.8 units of Mn-dependant peroxidase when it was cultured for 12 hours on the basic medium, and 8.9 units when it was cultured for 24 hours.

Example 4: Degradation of Aromatic Compounds by Lignin Lyases

Degradation capacity of lignin lyases produced from the microorganism of the present invention on aromatic compounds was analyzed. Aromatic compounds used herein were vanillin, vanillic acid, guanicol, phenol and p-coumaric acid as lignin monomer compounds and dealkaline lignin as a dimmer compound. Each aromatic compound was added to LB medium at each amount of 200 μg/ml, after which the microorganism of the present invention was cultured according to the time change. With the obtained culture supernatant thereby, the degradation rate of aromatic compounds was measured according to the production of lignin lyases. The degradation rate was determined by measuring absorbance at 275 nm, representing the decreased amount of aromatic compounds with the laps of time comparing with the amount of that before culturing.

Figure 2:
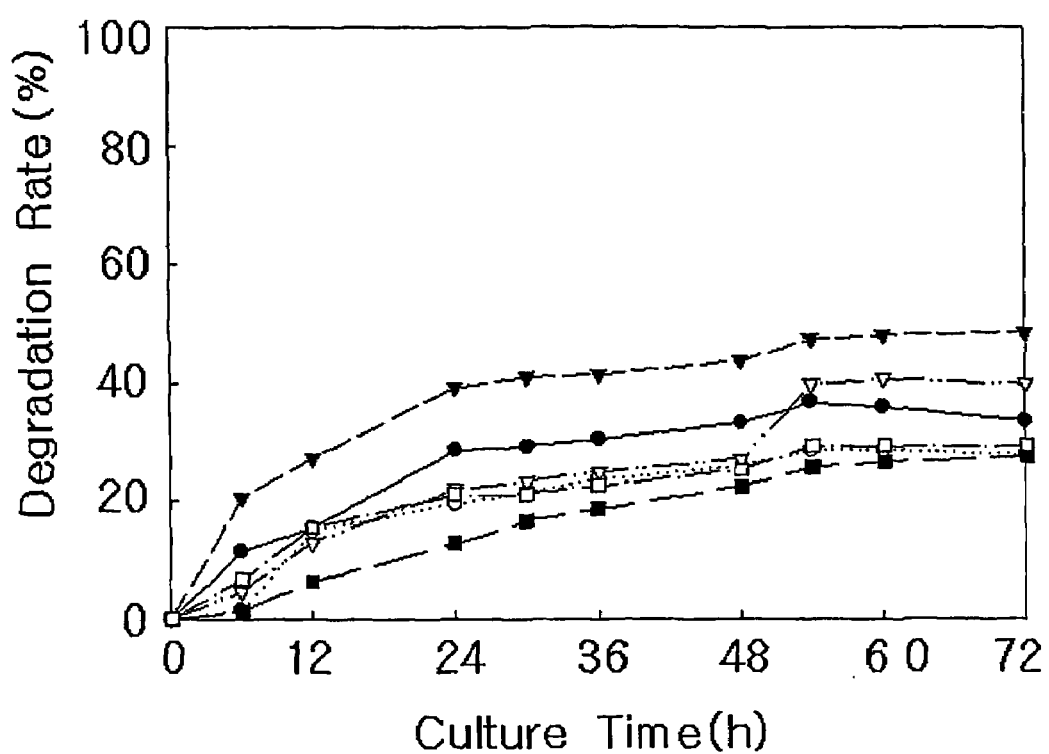
FIG. 2 is a graph showing the degradation ratio of aromatic compounds by lignin lyases produced by the microorganism of the present invention.
●: dealkaline lignin, ○: vanillic acid,
▼: vanillin, ∇: guaiacol,
■: ρ-coumaric acid, □: phenol

As a result, lignin lyases produced by the microorganism of the present invention showed generally 20–45% of degradation capacity upon aromatic compounds overall, and the highest degradation capacity especially upon vanillin. Therefore, it was confirmed that the microorganism of the present invention produced lignin lyases which could effectually resolve degradation-difficult aromatic compounds (FIG. 2).

Example 5: Production of Lignin Lyases by the Microorganism of the Present Invention <5-1> Culture Media of the Present Invention The present inventors used LB medium (0.5% yeast extract, 1% tryptone, 1% NaCl) or M9 medium (1% $Na_2HPO_4$, 0.3% $KH_2PO_4$, 0.05% NaCl, 0.1% $NH_4Cl$) for culturing the microorganism of the present invention. Since the microorganism had grown slowly and produced less lignin lyases on the basic LB or M9 medium, another medium based on M9 was specially formed in order for the microorganism to produce lignin lyases more effectively. The medium was formed by adding 0.5% yeast extract, 0.5% tryptone, 1% cellulose and 1% xylose to basic M9 medium. The medium was autoclaved at 120° C. for 20 minutes, after which the microorganism of the present invention was cultured for 25–30 hours with 180 rpm at 37° C. Then, supernatant was obtained by centrifugation (12,000 rpm, 5 min.). The amount of lignin lyases and microorganism of each LB medium, M9 medium and the specially formed medium are as follows (Table 3).

TABLE 3

| Medium | Amount of Microorganism ($OD_{550}$) | Amount of Lignin Lyases (units/ml) | | |
|---|---|---|---|---|
| | | Laccase | Lignin Peroxidase | Mn-dependant Peroxidase |
| M9 | 0.1 | 174 | 1.1 | 2.7 |
| LB | 4.2 | 324 | 10.8 | 64.9 |
| M9* | 8.6 | 1374 | 26.5 | 140.8 |

M9*: specially formed medium

In case of laccase, the enzyme activity in the specially formed medium increased four-fold than that of in LB medium and seven-fold than that of in M9 medium. Lignin peroxidase activity in the specially formed medium increased 1.5-fold than that of in LB medium and 25-fold than that of in M9 medium, while Mn-dependent-peroxidase activity in the specially formed medium showed the 2.2-fold increase than that of in LB medium and 70-fold increase than that of in M9 medium.

<5-2> Enhancement of Laccase Production

Figure 3:
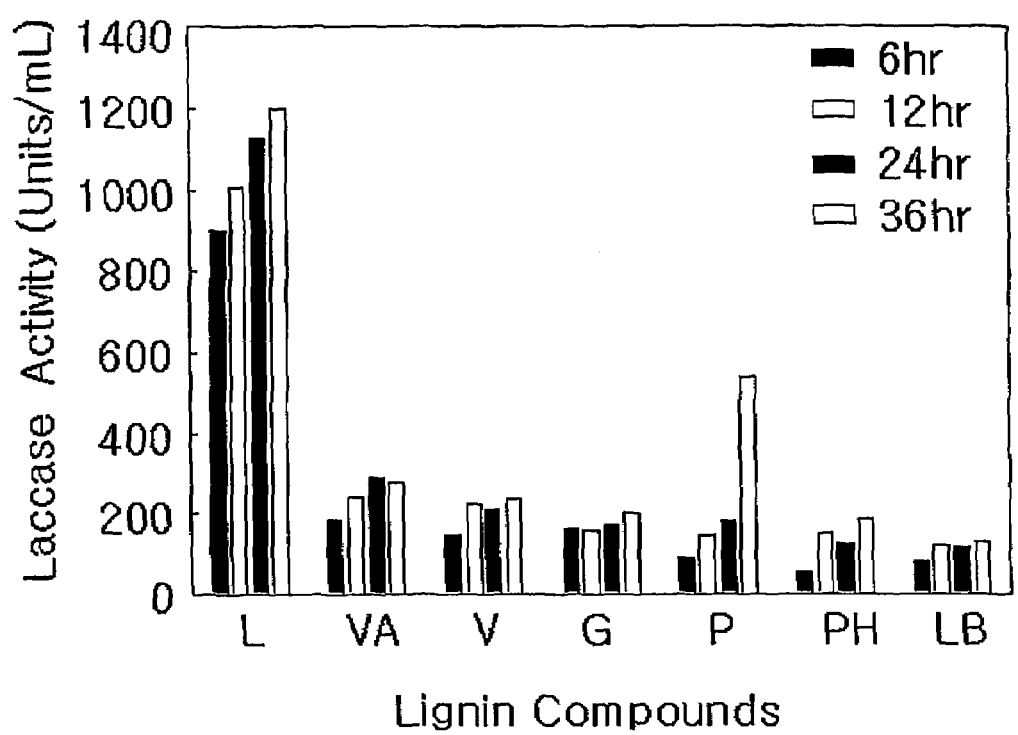
FIG. 3 is a graph showing the acceleration of laccase production by adding aromatic compounds.
L : dealkaline lignin, VA: vanillic acid,
V: vanillin, G: guaiacol,
ρ: ρ-coumaric acid, PH: phenol,
LB: LB medium

After each aromatic compound was added in the manner of example <3-1>, the laccase activity was measured. As a result, it was confirmed that the laccase activity was increased by lignin dimmer compound. Dealkaline lignin, a dimmer compound, induced the laccase activity by almost two-fold than other lignin compound did (FIG. 3).

<5-3> Enhancement of Lignin Peroxidase Production

After each aromatic compound was added in the manner of example <3-2>, the lignin peroxidase activity was measured. As a result, lignin peroxidase showed 7 fold higher activity when ρ-coumaric acid was added comparing with the cases that other aromatic compounds were added (FIG. 4).

<5-4> Enhancement of Mn-dependent Peroxidase Production

After each aromatic compound was added in the manner of example <3-3>, the Mn-dependent peroxidase activity was measured. As a result, Mn-dependent peroxidase showed 1.5 fold higher activity when vanillin or vanillic acid was added, while it showed no changes when guaiacol or phenol was added (FIG. 5).

INDUSTRIAL APPLICABILITY

As shown above, the microorganism of the present invention produces one or more of lignin lyases, such as laccase, lignin peroxidase and Mn-dependent peroxidase, by which the microbe can be used not only in the treatment of industrial sewage and harmful environmental substance but also in oil degradation, in biological bleaching of pulp. Moreover, the microbe can also be used effectively in industry of preparing fuel, forage and other chemicals through lignin degradation.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. An isolated *Serratia marcescens* HY-5 which is deposited under accession NO: KCTC 1009BP.

2. The isolated *Serratia marcescens* HY-5 according to claim 1, which produces laccase, lignin peroxidase and Mn-dependent peroxidase.

3. The isolated *Serratia marcescens* HY-5 according to claim 1, which is isolated from gut of *Sympetrum depressiusulm*.

* * * * *

UNITED STATES PATENT AND TRADEMARK OFFICE
CERTIFICATE OF CORRECTION

| | | |
|---|---|---|
| PATENT NO. | : 7,083,968 B2 | Page 1 of 1 |
| APPLICATION NO. | : 10/481233 | |
| DATED | : August 1, 2006 | |
| INVENTOR(S) | : Ho Yong Park et al. | |

It is certified that error appears in the above-identified patent and that said Letters Patent is hereby corrected as shown below:

At item (73) on the Title page of the patent, the second assignee --Korea Research Institute of Bioscience and Biotechnology (KR)-- should be added.

Signed and Sealed this

Twenty-sixth Day of June, 2007

JON W. DUDAS
*Director of the United States Patent and Trademark Office*